(12) United States Patent
Perouse (10) Patent No.: US 8,361,137 B2
(45) Date of Patent: Jan. 29, 2013

(54) TUBULAR PROSTHESIS

(75) Inventor: Eric Perouse, Paris (FR)

(73) Assignee: Laboratoires Perouse, Ivry le Temple (FR)

( * ) Notice: Subject to any disclaimer, the term of this patent is extended or adjusted under 35 U.S.C. 154(b) by 408 days.

(21) Appl. No.: 10/588,489

(22) PCT Filed: Feb. 9, 2005

(86) PCT No.: PCT/FR2005/000291
§ 371 (c)(1),
(2), (4) Date: Aug. 4, 2006

(87) PCT Pub. No.: WO2005/079705
PCT Pub. Date: Sep. 1, 2005

(65) Prior Publication Data
US 2007/0043432 A1    Feb. 22, 2007

(30) Foreign Application Priority Data

Feb. 11, 2004  (FR) ...................................... 04 01366

(51) Int. Cl.
*A61F 2/06* (2006.01)
(52) U.S. Cl. ..................................... 623/1.15; 623/1.13
(58) Field of Classification Search ................... 623/1.1, 623/1.11, 1.15, 1.16, 1.49–1.54, 1.36, 1.23, 623/1.13; 606/213, 219, 151, 155, 144, 157, 606/158, 108, 192, 194
See application file for complete search history.

(56) References Cited

U.S. PATENT DOCUMENTS

| | | | |
|---|---|---|---|
| 5,443,496 A * | 8/1995 | Schwartz et al. | 623/1.16 |
| 5,591,226 A * | 1/1997 | Trerotola et al. | 623/1.12 |
| 5,720,755 A | 2/1998 | Dakov | |
| 5,976,178 A * | 11/1999 | Goldsteen et al. | 623/1.13 |
| 6,030,392 A | 2/2000 | Dakov | |
| 6,117,167 A * | 9/2000 | Goicoechea et al. | 623/1.16 |
| 6,206,911 B1 | 3/2001 | Milo | |
| 6,254,618 B1 | 7/2001 | Dakov | |
| 6,451,048 B1 * | 9/2002 | Berg et al. | 623/1.13 |
| 6,485,513 B1 * | 11/2002 | Fan | 623/1.36 |
| 6,984,244 B2 * | 1/2006 | Perez et al. | 623/1.23 |
| 6,994,713 B2 * | 2/2006 | Berg et al. | 606/153 |
| 7,267,682 B1 * | 9/2007 | Bender et al. | 606/219 |
| 2001/0014822 A1 | 8/2001 | Milo | |
| 2002/0123790 A1 | 9/2002 | White et al. | |
| 2003/0018377 A1 * | 1/2003 | Berg et al. | 623/1.11 |
| 2005/0102024 A1 | 5/2005 | Riccotta et al. | |

FOREIGN PATENT DOCUMENTS

| | | |
|---|---|---|
| WO | 00/07506 | 2/2000 |
| WO | 02/085254 | 10/2002 |

* cited by examiner

*Primary Examiner* — Kathleen Sonnett
*Assistant Examiner* — Jocelin Tanner
(74) *Attorney, Agent, or Firm* — Wenderoth, Lind & Ponack, L.L.P.

(57) ABSTRACT

The radially deformable tubular prosthesis comprises a lattice that is deformable between a retracted state of small diameter and an expanded state of greater diameter. It includes at least two external hooks defining between them a clamp for hooking in external tissue, the two hooks being carried by the lattice and being movable between a spaced-apart position in which the clamp is open, and a closer-together position in which the clamp is closed.

18 Claims, 7 Drawing Sheets

TUBULAR PROSTHESIS

BACKGROUND OF THE INVENTION

The present invention relates to a tubular prosthesis of the type that is radially deformable, comprising a lattice that is deformable between a retracted state of small diameter and an expanded state of larger diameter.

For various types of treatment, it is known to place a tubular prosthesis inside a blood vessel, whether a vein or an artery. Such tubular prostheses are generally referred to by the term "stent".

The prosthesis is brought to the inside of the vessel while it is in its retracted state, and then for positioning purposes, the prosthesis is expanded so as to press against the inside surface of the vessel. This expansion is performed either automatically because of the elasticity of the prosthesis lattice, or else under drive from an internal balloon being inflated, leading to plastic deformation of the material constituting the lattice.

It is difficult to ensure that the prosthesis is held axially within the vessel, i.e. in the long direction of the vessel, and the prosthesis runs the risk of being moved along the vessel under drive from the flow of blood. In addition, the prosthesis runs the risk of not being pressed exactly against the surface of the blood vessel, because of its irregular section.

In order to avoid such movement, it is known that the end of the metal lattice can have outwardly-projecting catches suitable for penetrating into the wall of the vessel so as to prevent the prosthesis from moving axially.

It is also known to secure the prosthesis to the wall of the vessel, e.g. by putting clips into place, which clips are fitted after the prosthesis has been put into place.

Those fastener means are not very reliable and they are difficult to put into place.

SUMMARY OF THE INVENTION

An object of the invention is to provide a tubular prosthesis which can be positioned reliably and which is relatively easy to put into place.

To this end, the invention provides a tubular prosthesis of the above-specified type. The prosthesis includes at least two external hooks defining between them a clamp for hooking in external tissue, the two hooks being carried by the lattice and being movable between a spaced-apart position in which the clamp is open, and a closer-together position in which the clamp is closed.

In particular embodiments, the tubular prosthesis includes one or more of the following characteristics:

- each hook is connected to the lattice from a connection end, and the hooks of a given clamp are movable relative to each other during deformation of the prosthesis;
- the lattice comprises crossing wires that form meshes in the form of deformable quadrilaterals, and each hook is connected to the lattice in a corner of a quadrilateral;
- each hook is welded or soldered to the lattice at its connection end;
- each hook is extended at its connection end by a strand that is twisted around the lattice;
- each hook of a given clamp presents the shape of a shepherd's crook at its hooking end, the two hooks overlapping at least in part in order to form the clamp;
- each hook is in the form of a substantially rectilinear blade, the two hooks extending facing each other and spaced apart from each other when the clamp is open; and
- the lattice is elastically deformable towards its expanded position.

The invention also provides a kit for treating a blood vessel, the kit being characterized in that it comprises:

- a prosthesis as defined above;
- means for holding the lattice in the retracted state in the region of each clamp; and
- a lattice-delivery tube defining a confinement duct for confining the prosthesis in its retracted state.

In a particular embodiment, the confinement duct of the delivery tube includes longitudinal channels for receiving the hooks.

BRIEF DESCRIPTION OF THE DRAWINGS

The invention can be better understood upon reading the following description given purely by way of example and made with reference to the drawings, in which.

DETAILED DESCRIPTION OF THE INVENTION

Figure 1:
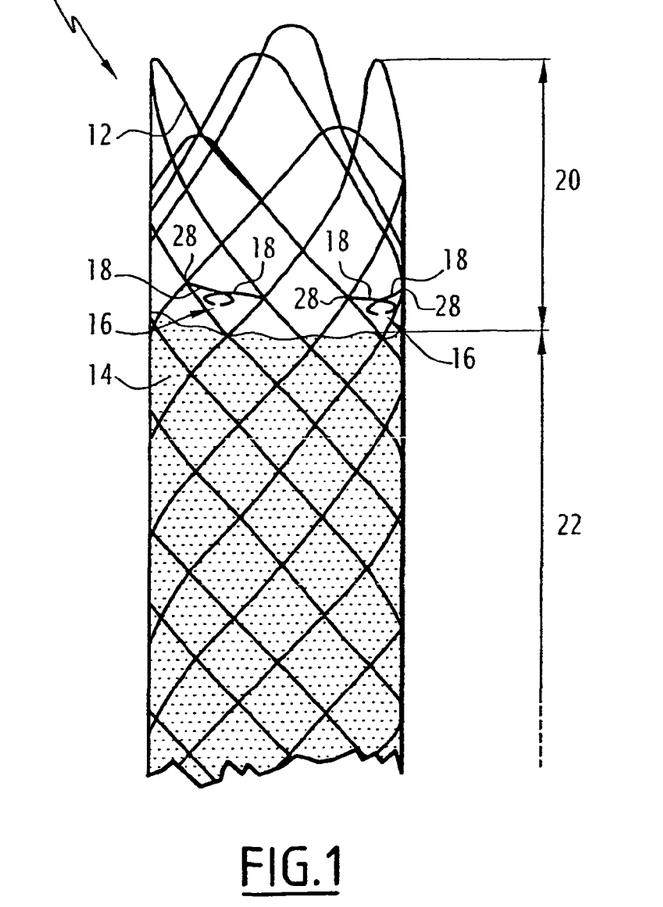
FIG. 1 is a perspective view of a tubular prosthesis in the expanded state.

The tubular prosthesis 10 shown in FIG. 1 is to be put into place in a blood vessel. It comprises a tubular lattice 12 that is embedded in a film 14 over substantially the entire length of the prosthesis. In the vicinity of one of its ends, the prosthesis also comprises three clamps 16 that are angularly spaced apart regularly at (evenly around) its periphery.

Each clamp 16 is made up of two hooks 18 carried by the metal lattice 12. These hooks can be moved relative to each other between a spaced-apart position in which the clamp is open, and a close-together position in which the clamp is closed.

The clamps 16 are provided on an end segment 20 of the prosthesis that does not have any film 14, the lattice 12 thus not being covered in this region. In contrast, the main segment of the prosthesis, indicated by reference number 22, has the lattice 12 embedded in the film 14.

The lattice 12 is made of stainless steel of biocompatible quality. For example, it is made by braiding or knitting a wire, axially expanding a tube, or by any other suitable technique.

In the embodiment shown in FIG. 1, the lattice 12 is constituted by two bundles of wires wound helically in opposite directions, the wires in any one bundle generally extending parallel to one another and across the wires of the bundle of wires that are wound in the opposite direction to form meshes.

The wires in the two oppositely-wound bundles cross over and under one another in alternation.

The lattice 12 is preferably elastically deformable to expand radially between a small diameter retracted state and a larger diameter expanded state.

In its expanded state, shown in FIG. 1, the meshes of the lattice form lozenges that are generally elongated in the circumferential direction (i.e., circumferentially-elongated lozenge-shaped meshes). In contrast, and as shown in FIG. 3B, when the prosthesis is in the retracted state, the meshes form lozenges that are elongated parallel to the axis of the prosthesis (i.e., axially elongated logenge-shaped meshes).

In a variant, the prosthesis is plastically deformable, i.e. the lattice presents a first stable shape of small diameter and a second stable shape of larger diameter.

Over its main segment 22, the lattice 12 is completely embedded in the film 14. This film is constituted by a material that is stretchable and liquid-proof, and it fills the meshes.

This material is sufficiently stretchable to enable the film 14 to follow the deformation of the lattice from its retracted state to its expanded state without tearing or becoming unstuck, and in spite of the meshes of the lattice deforming. Suitable materials are biocompatible elastomers such as a natural or synthetic rubber or indeed a biocompatible polymer such as a polyurethane.

The lattice 12 can be coated with the film 14 by a co-extrusion technique or a dipping technique, after the metal has been degreased and treated with a bonding primer.

Figure 2:
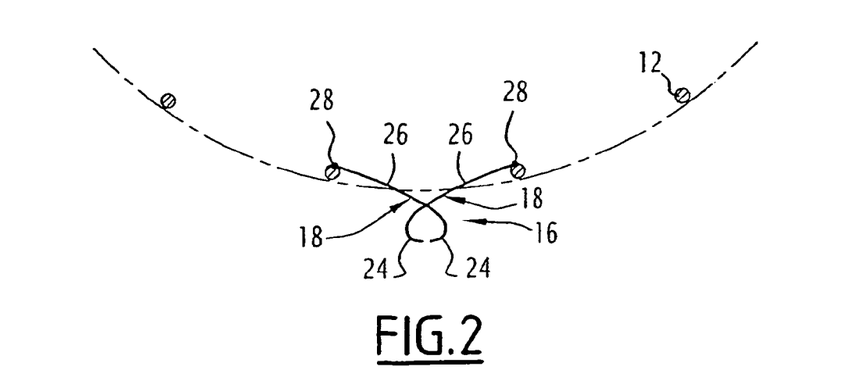
FIG. 2 is a section view on a larger scale showing the prosthesis in the expanded state in a region that includes a clamp.

As shown in FIG. 2, each of the hooks 18 forms a metal wire segment having a free end that is curved outwards to form the shape of a shepherd's crook 24. The crook 24 extends a rectilinear segment 26. The hooks 18 overlap at least in part in order to form a clamp 16.

At its end opposite from the crook 24, each segment 26 is bonded to the metal lattice 12 in the opposite corners of a mesh by weld or solder tacking 28, visible in FIG. 1. The crooks 24 project outwards from the tubular segment defined by the lattice 12, and, at rest, the curved ends of the crooks lie in a plane extending transversely to the tubular prosthesis, i.e. perpendicular to its general (central) axis, as can be seen in FIG. 2.

The diameter of the crooks 24 forming the hooks lies in the range 0.5 millimeters (mm) to 4 mm, whereas the length of the arms 26 lies in the range 3 mm to 12 mm. The crooks 24 forming the curved ends of the hooks preferably have a diameter lying in the range one-fourth to one-eighth the length of the arm 26 of the hook.

The length of the arms 26 is such that when the prosthesis is in the expanded state as shown in FIG. 1, the two crooks of the hooks 18 are moved towards each other and together define a loop that is closed or practically closed.

Figure 3A:
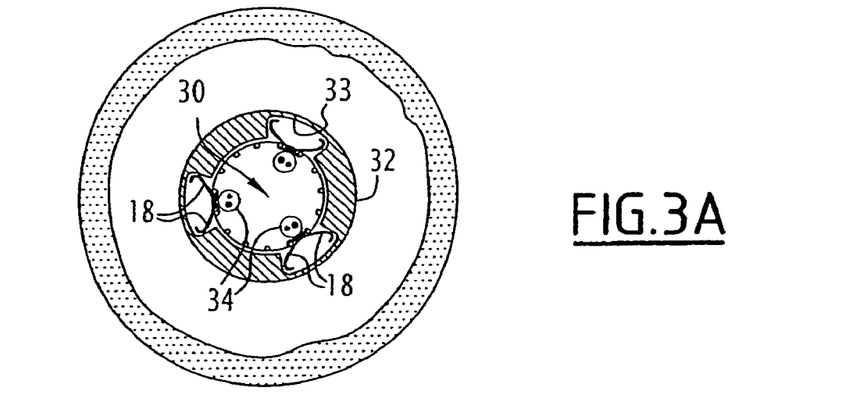
FIG. 3A is a cross-section view of the prosthesis in the retracted state.
Figure 3B:
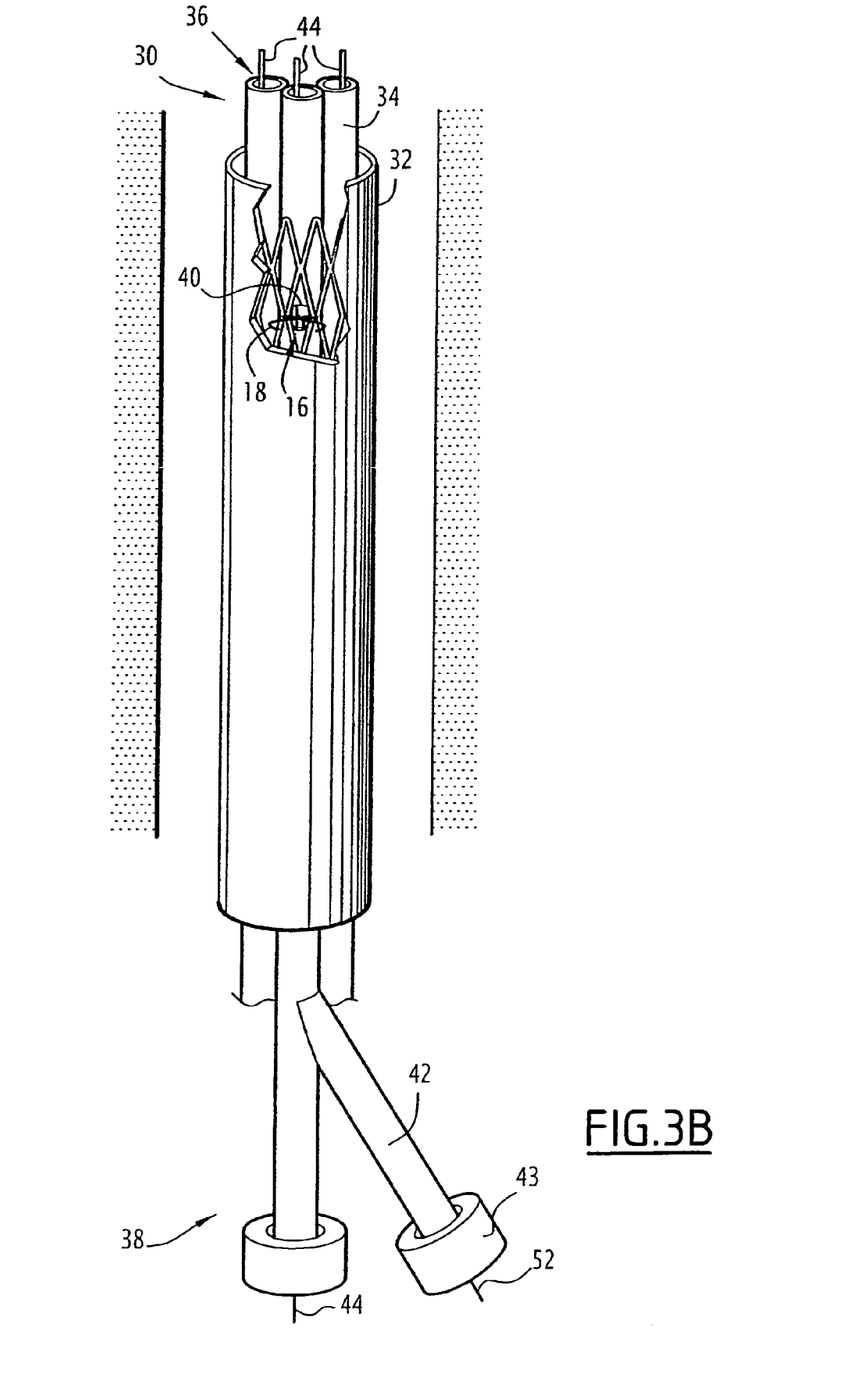
FIG. 3B is a perspective view of the prosthesis being implanted while in the retracted state of FIG. 3.
Figure 3C:
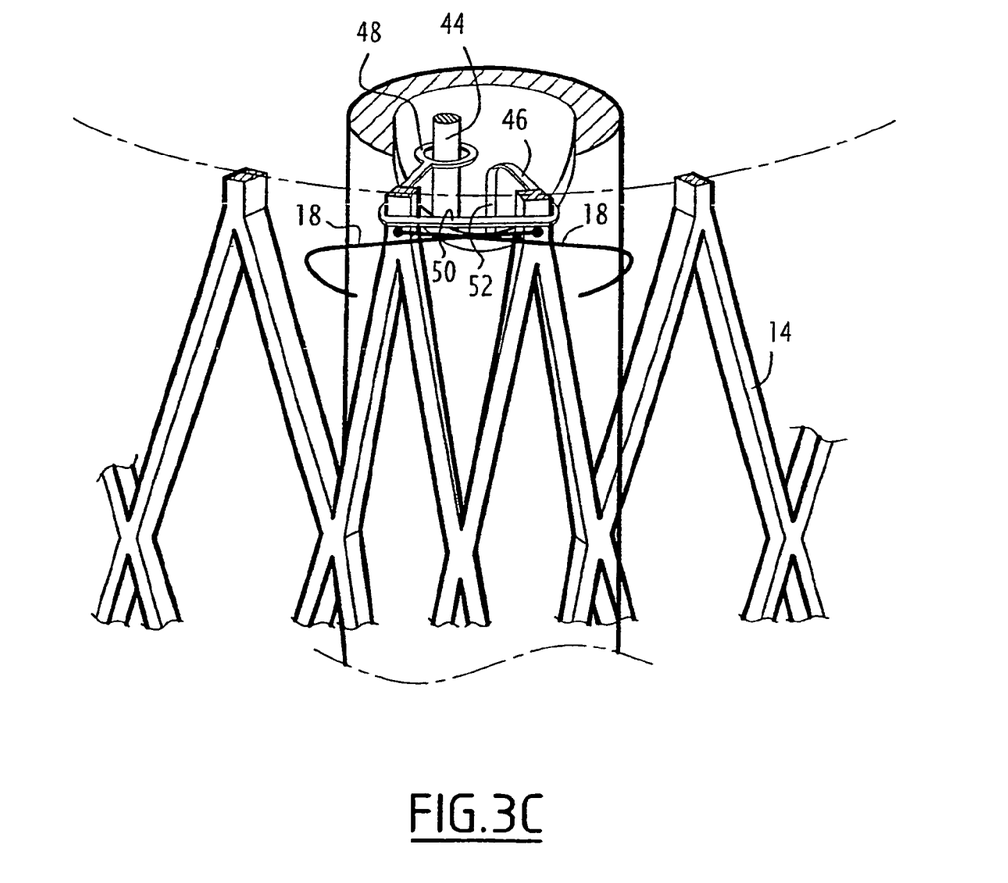
FIG. 3C is a section view on a larger scale showing the prosthesis in the retracted state in a region that includes a clamp in the open position.

Initially, and as shown in FIGS. 3A, 3B, and 3C, the prosthesis is associated with means (retaining device) 30 for retaining the clamps 16 in the open position.

In addition, the prosthesis having its clamps held open is received in a conventional manner in a delivery tube 32, within which the prosthesis is confined in its retracted state.

Advantageously, the inside duct of the tube 32 has longitudinal channels 33 for receiving the ends of the hooks 18 that project from the generally tubular surface of the metal lattice.

As shown in FIGS. 3B and 3C, each means for holding a clamp open comprises a flexible tube 34, e.g. made of polyether ether ketone (PEEK). The tube 34 extends longitudinally between a distal end 36 for being received in the blood vessel, and a proximal end 38 designed to be accessible to the surgeon outside the body of the patient. Thus, the tube 34 may be about 1 meter (m) long.

A retaining opening 40 is provided in the side of the tube 34 generally in register with (corresponding to) the associated clamp 16. The tube 34 is also fitted, in the vicinity of its proximal end 38, with a hollow side branch 42 fitted with a ring 43 for axially locking a sliding thread.

The releasable retaining device 30 also comprises a retaining rod 44 engaged axially in each tube 34, and a retaining thread 46 going round the mesh of the prosthesis that carries the clamp 16.

The retaining rod 44 extends from one end of the tube 34 to the other. It projects out from the tube at the proximal end 38.

This rod is movable inside the tube 34 between a retaining position, in which the rod faces the opening 40, and a release position, in which the rod 44 is spaced apart from the opening 40 and is offset towards the proximal end of the tube 34.

The retaining thread 46 comprises a single strand having an eyelet 48, a tightening loop 50, and a control segment 52 that extends along the entire length of the tube 34 from the opening 40 to the branch connection 42 from which it projects after passing through a locking ring 43.

The end eyelet 48 is constituted by a closed loop of small diameter through which the rod 44 is initially engaged when it is in its retaining position. The tightening loop 50 is formed by a strand segment engaged slidably through two meshes of the lattice adjacent to the mesh carrying the clamp 16.

The tightening loop passes through the opening 40 to join the eyelet 48 at one end and the control segment 52 at its other end. The active length of the tightening loop 50 is variable as a function of the traction exerted on the control segment 52, so that it controls the shape of the mesh carrying the clamp 16, as explained below.

Initially, prior to being put into place, the prosthesis is placed in the delivery tube 32, and the control segments 52 of the clamp-retaining device 30 are under tension such that the clamps are held open, as shown in FIG. 3B. In this position, the tightening loop 50 tightens the mesh carrying the clamp so that the lozenge-shaped mesh is elongated along its diagonal that is parallel to the axis of the prosthesis.

Figure 4A:
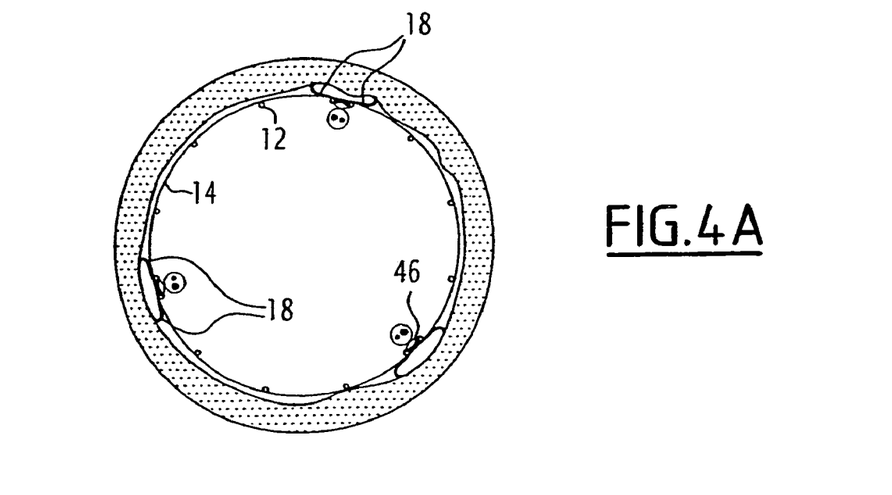
FIG. 4A is a view identical to that of FIG. 3A showing the prosthesis expanded prior to hooking.
Figure 4B:
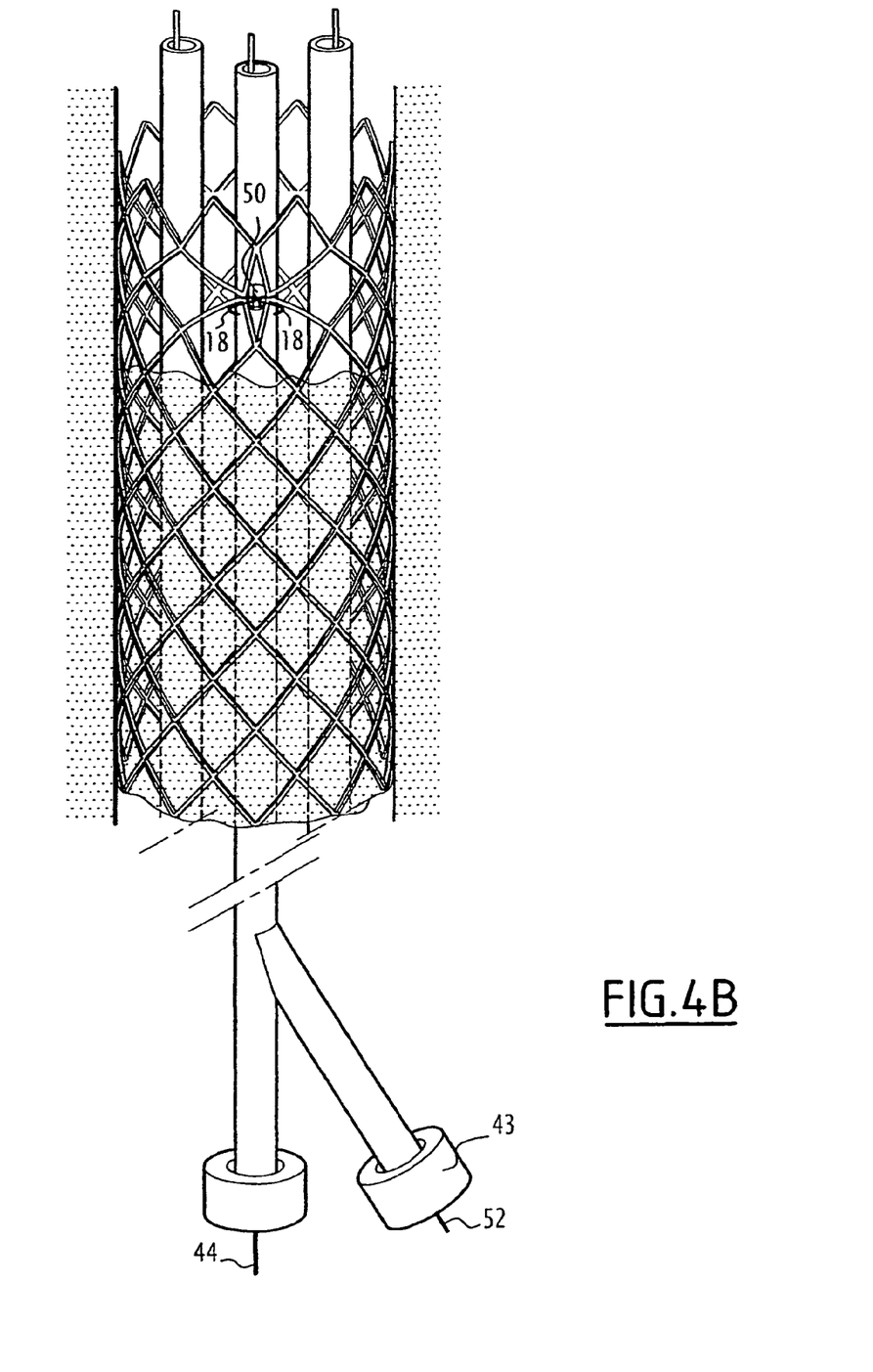
FIG. 4B is a perspective view of the expanded prosthesis prior to hooking.

To put the prosthesis into place, it is inserted together with the tube 32 into the delivery zone, and then the tube 32 is withdrawn, thereby releasing the prosthesis. The prosthesis expands and then becomes pressed against the inside surface of the blood vessel, as shown in FIGS. 4A and 4B.

During this expansion, the meshes of the prosthesis lattice extend because of the elasticity of the lattice so that the peripheral diagonal of the prosthesis lengthens, thus enabling the diameter of the prosthesis to be increased. In contrast, the meshes carrying clamps remain contracted, as shown in FIG. 4B, because of the tightening loops 50. Thus, the clamps 16 are docked against the surface of the blood vessel while they are still in the open position.

Figure 5A:
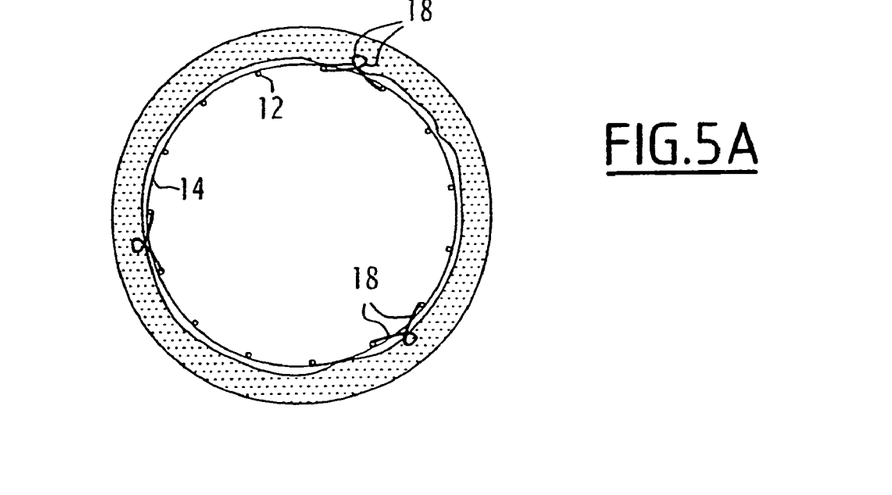
FIG. 5A is a view identical to FIG. 3A showing the prosthesis expanded and hooked after the clamp-retaining members have been withdrawn.
Figure 5B:
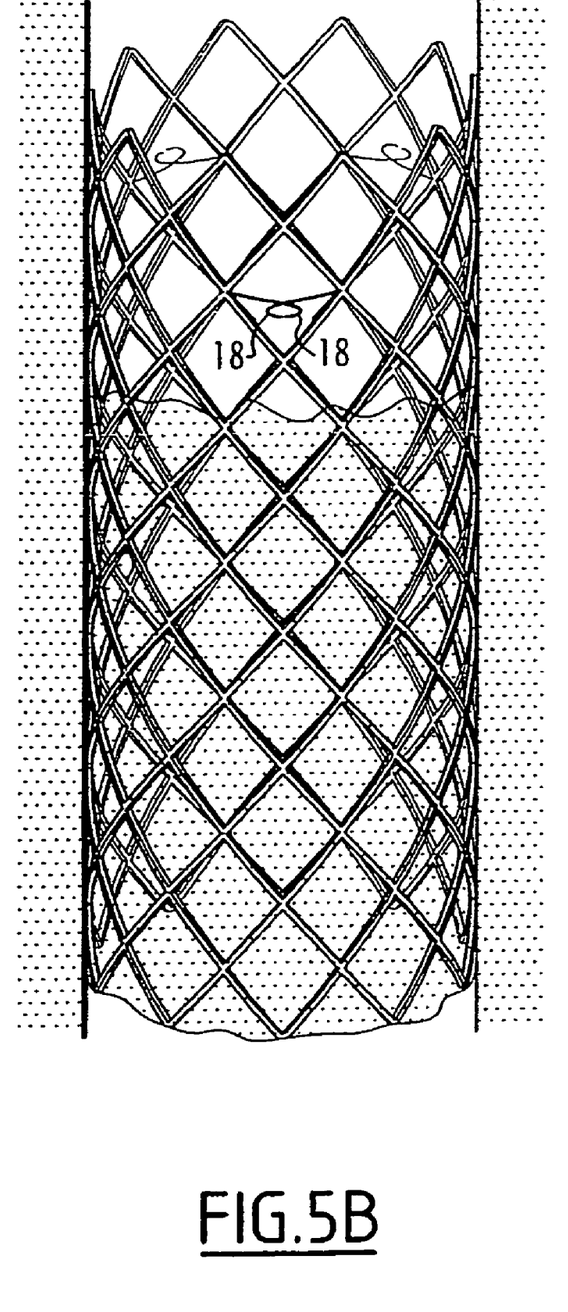
FIG. 5B is a perspective view of the expanded prosthesis after the clamp-retaining members have been withdrawn.

By acting on the locking ring 43, the practitioner then proceeds to release the retaining thread 46 so as to allow the meshes carrying the clamps to deform elastically, thereby causing pairs of opposite hooks to move towards each other, closing each clamp, and causing the hooks to penetrate into the wall defining the blood vessel, as shown in FIGS. 5A and 5B.

After the retaining threads 46 have been released, the rod 44 is brought into the release position, such that the eyelet 48 is released from the rod 44. The practitioner then pulls on the control segment 52, enabling the retaining thread to escape from the metal lattice, traveling through the two meshes adjacent to the mesh carrying the clamp.

Thus, since the clamp-retaining device have been made independent of the prosthesis, they can be extracted along an endoluminal path.

It will be understood that such a prosthesis is held effectively against the inside surface of the vessel by the presence of the clamps being held elastically in the closed position under drive from the prosthesis. In addition, since the clamps are closed simultaneously with the prosthesis being put into place, it is relatively easy to install such a prosthesis.

Figures 6, 7:
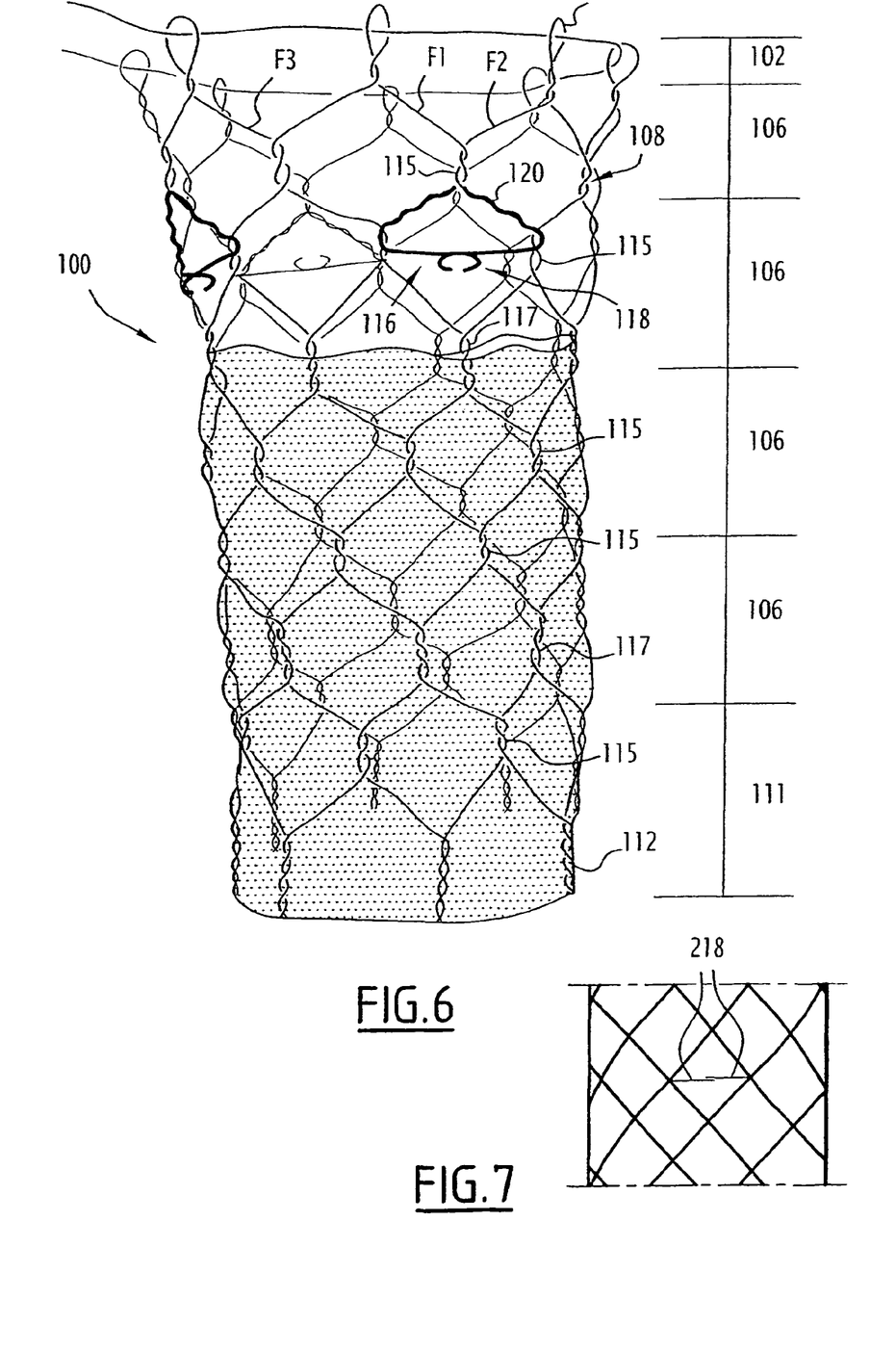
FIGS. 6 and 7 are perspective and elevation views of various embodiments of the prosthesis of the invention.

FIG. 6 shows a variant embodiment of a prosthesis of the invention.

The vascular prosthesis shown in FIG. 6 comprises a lattice 100 itself made up of eight elastic metal wires, such as the wires F1, F2, and F3, that are twisted together in a manner that is described in greater detail below. Along the length of the lattice, these wires define a plurality of successive regions, which going downwards in FIG. 6 are as follows:

an end zone 102 having eight loops 104;
successive middle regions 106, each presenting peripheral rings of twisted nodes 108;
an end region 111 having end twists 112.
Considering the wire F1:
the loop 104 is constituted by the wire F1 twisted into a loop over at least half a turn; and
each node 108 is constituted by a twist of the wire F1 together with an adjacent wire such as F2 or F3 over one or more turns.

Thus, on either side of each double-twisted node referenced 115 where the wire is twisted through an even number of half-turns, and in particular through two half-turns, each wire strand forming the node extends in two directions that are parallel to each other and close together.

In contrast, with so-called triple-twisted nodes 117 where the wire is twisted through an odd number of half-turns, in particular three half-turns, each wire leaves in two directions that form between them an angle that is much less than 180°, for example a right angle or even an acute angle as shown, so as to constitute two adjacent sides of one of the meshes of the lattice.

As shown in FIG. 6, in the example shown, the wire F1 starts from a twist 112 and then forms successively a node 115, a node 117, a node 115, another node 115, a node 117, a node 115, another node 115, a loop 113, a node 115, another node 115, a node 117, a node 115, another anode 115, a node 117, a node 115, and another twist 112.

In this embodiment, each clamp referenced 116 is formed by a single metal wire 120 whose middle portion is engaged and twisted around wires defining the lattice, and whose two free ends are curved outwards to form hooks 118.

More precisely, the wire 120 is twisted from a node 115 about two angularly offset strands that diverge. Each branch of the wire 120 is then twisted with the following twisted node and thereafter extends transversely along a mesh diameter, the two arms meeting by extending parallel to each other towards respective curved ends.

Thus, as in the preceding embodiment, it is deformation of the mesh carrying the clamp that causes the clamp to open or close, the two arms with curved ends moving relative to each other.

In the embodiment of FIG. 7, the hooks 218 are formed by simple, generally-rectilinear rods, each having one end secured to the end of a mesh and its other end projecting outwards a little from the generally cylindrical outside surface of the lattice.

In this embodiment, when the meshes are open, the pointed ends of two hooks 218 overlap. However, when the two adjacent meshes disposed on either side of the mesh carrying the clamp are closed, then the hooks are spaced apart from each other.

In order to put such a prosthesis into place, it is necessary to have two means for holding meshes closed for each of the clamps. Initially, they are applied to the two adjacent meshes so as to enable the clamp to be held open. After the prosthesis has been properly positioned, the two adjacent meshes are released, thereby leading to the clamp closing and the two hooks penetrating into the wall of the blood vessel.

The invention claimed is:

1. A radially deformable endovascular prosthesis, comprising:
a lattice deformable between a retracted state wherein said lattice has a small diameter, and an expanded state wherein said lattice has a large diameter;
a pair of external hooks having crook portions configured to define a clamp for anchoring said prosthesis to external tissue, said pair of hooks being mounted to said lattice so as to be movable between a spaced-apart position wherein said crook portions are spaced apart such that said clamp is open, and a close-together position wherein said crook portions are close together such that said clamp is closed;
wherein said lattice includes crossed wires arranged to define meshes, said pair of hooks being connected to said wires of said lattice at opposite sides of one of said meshes of said lattice and are configured such that said pair of hooks cross each other, said lattice having a tubular shape, said pair of hooks being offset circumferentially with respect to each other around said tubular lattice, said lattice and said pair of hooks being configured such that said one of said meshes has a first shape when said lattice is in said retracted state so that said pair of hooks of said clamp are in said spaced-apart position, and such that said one of said meshes has a second shape when said lattice is in said expanded state so that said pair of hooks of said clamp are in said close-together position.

2. The prosthesis according to claim 1, wherein each hook of said pair of hooks has a connection end connected to said lattice, and said pair of hooks are configured to move relative to each other during deformation of said lattice from said refracted state to said expanded state.

3. The prosthesis according to claim 2, wherein each of said meshes of said lattice is shaped as a deformable quadrilateral, and each hook of said pair of hooks is connected to said lattice at a respective corner of one of said quadrilateral-shaped meshes.

4. The prosthesis according to claim 2, wherein said connection end of each hook of said pair of hooks is welded or soldered to said lattice.

5. The prosthesis according to claim 2, wherein said connection end of each hook of said pair of hooks is extended by a strand twisted around said lattice.

6. The prosthesis according to claim 1 wherein said crook portions of said pair of hooks are shaped and arranged to at least partly overlap when said lattice is in said expanded state so as to form said clamp.

7. The prosthesis according to claim 1, wherein each hook of said pair of hooks is shaped as a rectilinear blade, said pair of hooks extending facing each other and spaced apart from each other when said lattice is in said expanded state.

8. The prosthesis according to claim 1, wherein said lattice is elastically deformable towards said expanded state.

9. The prosthesis according to claim 1, further comprising a stretchable and liquid-proof film, said lattice having a tubular shape and being embedded in said film.

10. The prosthesis according to claim 1, wherein said pair of hooks are offset circumferentially with respect to each other around said tubular lattice by a first circumferential spacing when said pair of hooks are in said spaced-apart position, and said pair of hooks are offset circumferentially with respect to each other around said tubular lattice by a second circumferential spacing when said pair of hooks are in said close-together position, said second circumferential spacing being smaller than said first circumferential spacing.

11. A kit for treating a blood vessel, said kit comprising:
a radially deformable endovascular prosthesis, including:
a lattice deformable between a retracted state wherein said lattice has a small diameter, and an expanded state wherein said lattice has a large diameter;
pair of external hooks having crook portions configured to define a clamp for anchoring said prosthesis to external tissue, said pair of hooks being mounted to said lattice so as to be movable between a spaced-apart position wherein said crook portions are spaced apart such that said clamp is open, and a close-together position wherein said crook portions are close together such that said clamp is closed;
wherein said lattice includes crossed wires arranged to define meshes, said pair of hooks being connected to said wires of said lattice at opposite sides of one of said meshes of said lattice and are configured such that said pair of hooks cross each other, said lattice having a tubular shape, said pair of hooks being offset circumferentially with respect to each other around said tubular lattice, said lattice and said pair of hooks being configured such that said one of said meshes has a first shape when said lattice is in said retracted state so that said pair of hooks of said clamp are in said spaced-apart position, and such that said one of said meshes has a second shape when said lattice is in said expanded state so that said pair of hooks of said clamp are in said close-together position;
a retaining device for holding said lattice in said retracted state at said clamp, said retaining device being configured to maintain said clamp open by tightening said one of said meshes carrying said pair of hooks; and
a lattice delivery tube defining a confinement duct in which said lattice is confined in said refracted state, said retaining device being separate from said lattice delivery tube such that said lattice is releasable from said lattice delivery tube to assume said expanded state while said one of said meshes carrying said pair of hooks remains tightened.

12. The kit according to claim 11, wherein said confinement duct of said delivery tube includes longitudinal channels for receiving said pair of hooks.

13. The kit according to claim 11, wherein each hook of said pair of hooks has a connection end connected to said lattice, and said pair of hooks are configured to move relative to each other during deformation of said lattice from said retracted state to said expanded state.

14. The kit according to claim 13, wherein each of said meshes of said lattice is shaped as a deformable quadrilateral, and each hook of said pair of hooks is connected to said lattice at a corner of one of said quadrilateral-shaped meshes.

15. The kit according to claim 13, wherein said connection end of each hook of said pair of air of hooks is welded or soldered to said lattice.

16. The kit according to claim 11, wherein said crook portions of said pair of hooks are shaped and arranged to at least partly overlap when said lattice is in said expanded state so as to form said clamp.

17. The kit according to claim 11, wherein each hook of said pair of hooks is shaped as a rectilinear blade, said pair of hooks extending facing each other and spaced apart from each other when said lattice is in said expanded state.

18. The kit according to claim 11, further comprising a stretchable and liquid-proof film, said lattice having a tubular shape and being embedded in said film.

* * * * *